United States Patent
Oh et al.

(10) Patent No.: US 6,710,445 B2
(45) Date of Patent: Mar. 23, 2004

(54) COPLANARITY INSPECTION SYSTEM OF PACKAGE AND METHOD THEREOF

(75) Inventors: Tae Seok Oh, Seoul (KR); Jong Hong Kim, Kyungki-do (KR)

(73) Assignee: Mirae Corporation, Chunan-si (KR)

( * ) Notice: Subject to any disclaimer, the term of this patent is extended or adjusted under 35 U.S.C. 154(b) by 0 days.

(21) Appl. No.: 10/295,892

(22) Filed: Nov. 18, 2002

(65) Prior Publication Data

US 2003/0096437 A1 May 22, 2003

(30) Foreign Application Priority Data

Nov. 21, 2001 (KR) ................. 10-2001-0072804

(51) Int. Cl.⁷ ............................................. H01L 29/40
(52) U.S. Cl. ....................... 257/734; 257/686
(58) Field of Search ................. 257/87, 734; 355/66; 438/626, 458; 385/14

(56) References Cited

U.S. PATENT DOCUMENTS

| | | | |
|---|---|---|---|
| 4,736,108 A | * 4/1988 | Comstock et al. | 250/559.34 |
| 5,608,264 A | * 3/1997 | Gaul | 257/734 |
| 5,618,752 A | * 4/1997 | Gaul | 438/626 |
| 5,646,067 A | * 7/1997 | Gaul | 438/458 |
| 5,682,062 A | * 10/1997 | Gaul | 257/686 |
| 6,207,550 B1 | 3/2001 | Hase et al. | 438/613 |
| 6,243,509 B1 | * 6/2001 | Chen | 385/14 |
| 6,252,252 B1 | * 6/2001 | Kunii et al. | 257/81 |
| 6,603,532 B2 | * 8/2003 | Tsuji et al. | 355/66 |

* cited by examiner

Primary Examiner—John Niebling
Assistant Examiner—Andre' Stevenson
(74) Attorney, Agent, or Firm—Fleshner & Kim, LLP

(57) ABSTRACT

A surface mounting device having a coplanarity inspection system is disclosed. The surface mounting device includes: a vision apparatus including a camera for picking an electronic component from a head and inspecting a position and an alignment state of the electronic components; a laser sensor including a light receiving part and a light emitting part for inspecting the coplanarity of the electronic components; a controller for controlling data obtained by the laser sensor; and a computer for computing the coplanarity by receiving the data outputted from the controller.

4 Claims, 7 Drawing Sheets

COPLANARITY INSPECTION SYSTEM OF PACKAGE AND METHOD THEREOF

BACKGROUND OF THE INVENTION

1. Field of the Invention

The present invention relates to a coplanarity inspection system of a package and a method thereof.

2. Description of the Background Art

A surface mounting apparatus comprises a base frame, an X-Y gantry, a head unit, a printed circuit board and a components supplying device. The X-Y gantry is assembled on the base frame and make the head unit move toward directions of X-Y shafts. The head unit being moved by the X-Y gantry picks up a component supplied from the components supplying device and then mounts the components to the printed circuit board transferred to a components mounting position. The printed circuit board mounted the components is transferred to the components mounting position by a transfer device of the printed circuit board.

The construction of the surface mounting apparatus being used for mounting the components to the printed circuit board 1 will be described in detail with reference to the accompanying drawings. FIG. 1 is a perspective view of a surface mounting apparatus in accordance with a conventional art and FIG. 2 is a plane view of a surface mounting apparatus of FIG. 1. As shown in FIGS. 1 and 2, the surface mounting apparatus 10 comprises a base frame 11, an X-Y gantry 12, plural head units 13 and 14, a printed circuit board transfer device 15 and a components supplying device 16.

The X-Y gantry 12 installed to a plane of the base frame 11 comprises a Y-shaft stator's frame 12a, a Y-shaft permanent magnet 12b, a Y-shaft rotator 12c, an X-shaft stator's frame 12d, an X-shaft permanent magnet 12e, an X-shaft rotator 12g. The Y-shaft permanent magnets 12b comprise a plurality of N and S polarities and are assembled to the inside wall of the Y-shaft stator's frame 12a and the X-shaft permanent magnets 12e comprise a plurality of N and S polarities and are assembled to the inside wall of the X-shaft stator's frame 12a. The Y-shaft rotator 12c is assembled to the inside of the Y-shaft stator's frame 12a assembled the Y-shaft permanent magnets 12b and the X-shaft rotator 12g is assembled to the inside of the X-shaft stator's frame 12d.

A back plate 12f is installed to the plane of the X-shaft rotator 12g and a first head unit 13 among plural head units 13 and 14 is installed to the plane of the back plate 12f. When an electrical signal is supplied to the X-shaft rotator 12g from the external, the first head unit 13 assembled to the plane of the back plate 12f is moved toward the direction of the X-shaft by the trust generated between the X-shaft rotator 12g and the X-shaft permanent magnet 12e. Here, the X-shaft rotator 12g comprises a plurality of armature coils (not shown). For making the first head unit 13 move toward the direction of the Y-shaft, the X-shaft stator's frame 12d is moved toward the direction of the Y-shaft.

For making the X-shaft stator's frame 12d move toward the direction of the Y-shaft, the X-shaft stator's frame 12d is formed integrally with the Y-shaft rotator 12c. The Y-shaft rotator 12c formed integrally with the X-shaft stator's frame 12d is assembled to the inside of the Y-shaft stator's frame 12a and when an electrical signal is supplied to the plurality of armature coils (not shown) assembled to the Y-shaft rotator 12c, a trust is generated between the armature coil and Y-shaft permanent magnet 12b, so the Y-shaft rotator 12c is moved toward the direction of the Y-shaft by the trust.

According to the movement of the Y-shaft rotator 12c, the X-shaft stator's frame formed integrally with the Y-shaft rotator 12c is moved toward the direction of the Y-shaft and so the first head unit 13 is moved toward the direction of the Y-shaft. With the same of the first head unit 13 moving toward directions of the X-Y shafts, the second unit 14 of the plural head units 13 and 14 is moved toward directions of the X-Y shafts with the same as the method in the first head unit 13. The first head unit 13 and the second head unit 14 moving toward the directions of the X-Y shafts mount the components to the printed circuit board transferred by the printed circuit board transfer device 15.

For mounting the components to the printed circuit board 1 by using the first and second head units 13 and 14, the first and second head units 13 and 14 first suck the components. The components are mounted to the components supplying device 16 with a state of a tape reel (not shown). The components supplied from the tape reel mounted to the components supplying device 16 is transferred and mounted to the printed circuit board 1 by the first and second head units 13 and 14.

For mounting the components to the printed circuit board 1 by the plural first and second head units 13 and 14, a position for mounting the components in the printed circuit board is first sensed. For this, a vision camera 17 is used. As shown in FIG. 2, the vision camera 17 is fixedly installed to a side of the head unit 14 for sensing the position of the components and moved simultaneously when moving the head unit 14, thereby sensing the position for mounting the components to the printed circuit board 1.

That is, the head unit installed to the X-Y gantry 12 performs picking of the components (electronic components) from the components supplying device 16 and the vision inspection through the vision camera 17 is also performed and thereafter the placing of the components is performed to the printed circuit board 1 positioned on a conveyor. As shown in FIGS. 4 and 5, the components 20 comprises a body 21 and a plurality of leads 22 arranged around the body 21, and the lead 22 comprises a protrusion portion 22a curved horizontally from the package body 21, an inclination portion 22b extended with slant of a predetermined angle downwardly from the protrusion portion 22a, and a pin portion 22c curved extendedly again horizontally from the inclination portion 22b.

When the leads 22 are mounted to the printed circuit board 1, in a case that an alignment state including position or direction, width and high and low satisfies the regulated conditions, an exact contact state can be obtained. However, if the above regulated conditions are not satisfied, there occurs a problem: when mounting the package to the printed circuit board 1, the lead 22 comes off the printed circuit board 1 and so a proper soldering can not be performed, so that it stands in a casual relation in badness of the components. That is, there is a problem that when mounting the components 2, the coplanarity of the components, as the cause of the badness of the components, can not be confirmed.

SUMMARY OF THE INVENTION

Accordingly, it is a primary object of the present invention to solve the above problems.

Another object of the present invention is to provide a coplanarity inspection system of a package in which an error on an X-Y gantry is inspected and corrected by using a vision apparatus, and simultaneously the coplanarity of the components is inspected and corrected by a coplanarity inspection apparatus, and then the components is mounted, thereby capable of performing smoothly the components mounting work without a badness of the components.

In one aspect of the present invention, to achieve the above-described objects of the invention, in a surface mounting device for picking the electronic components from an electronic component feeding apparatus and then placing the components to a printed circuit board, the surface mounting device comprises: a vision apparatus including a head unit for picking an electronic component from a head and a camera for inspecting a position and an alignment state of the electronic components; a laser sensor including a light receiving part and a light emitting part for inspecting the coplanarity of the electronic components; a controller for controlling data obtained by the laser sensor; and a computer for computing the coplanarity by receiving the data outputted from the controller.

In another aspect of the present invention, there is provided a method for inspecting coplanarity of electronic components comprises: a first step for picking the electronic components from a component supplying apparatus by using a head unit, making the components move toward a vision apparatus, inspecting X and Y shafts of the electronic components, confirming a position and an alignment state of the components and then determining a scan path; a second step for making the electronic components move toward a position capable of inspecting and then scanning leads of the components; and a third step for inspecting the Z-shafts of the electronic components and then inspecting the coplanarity of the components by processing the inspected data of the respective leads by algorithm.

BRIEF DESCRIPTION OF THE DRAWINGS

The present invention will become better understood with reference to the accompanying drawings which are given only by way of illustration and thus are not limitative of the present invention, wherein.

DETAILED DESCRIPTION OF THE PREFERRED EMBODIMENTS

A coplanarity inspection apparatus in accordance with preferred embodiments of the present invention will now be described in detail with reference to the accompanying drawings.

Figure 1:
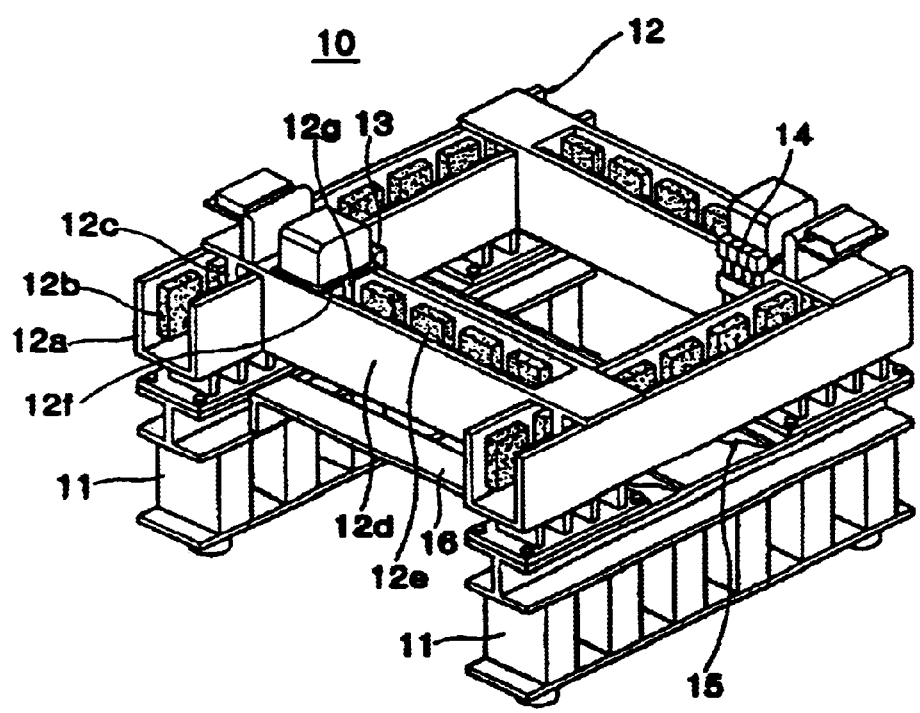
FIG. 1 is a perspective view illustrating a surface mounting apparatus according to a conventional art.
Figure 2:
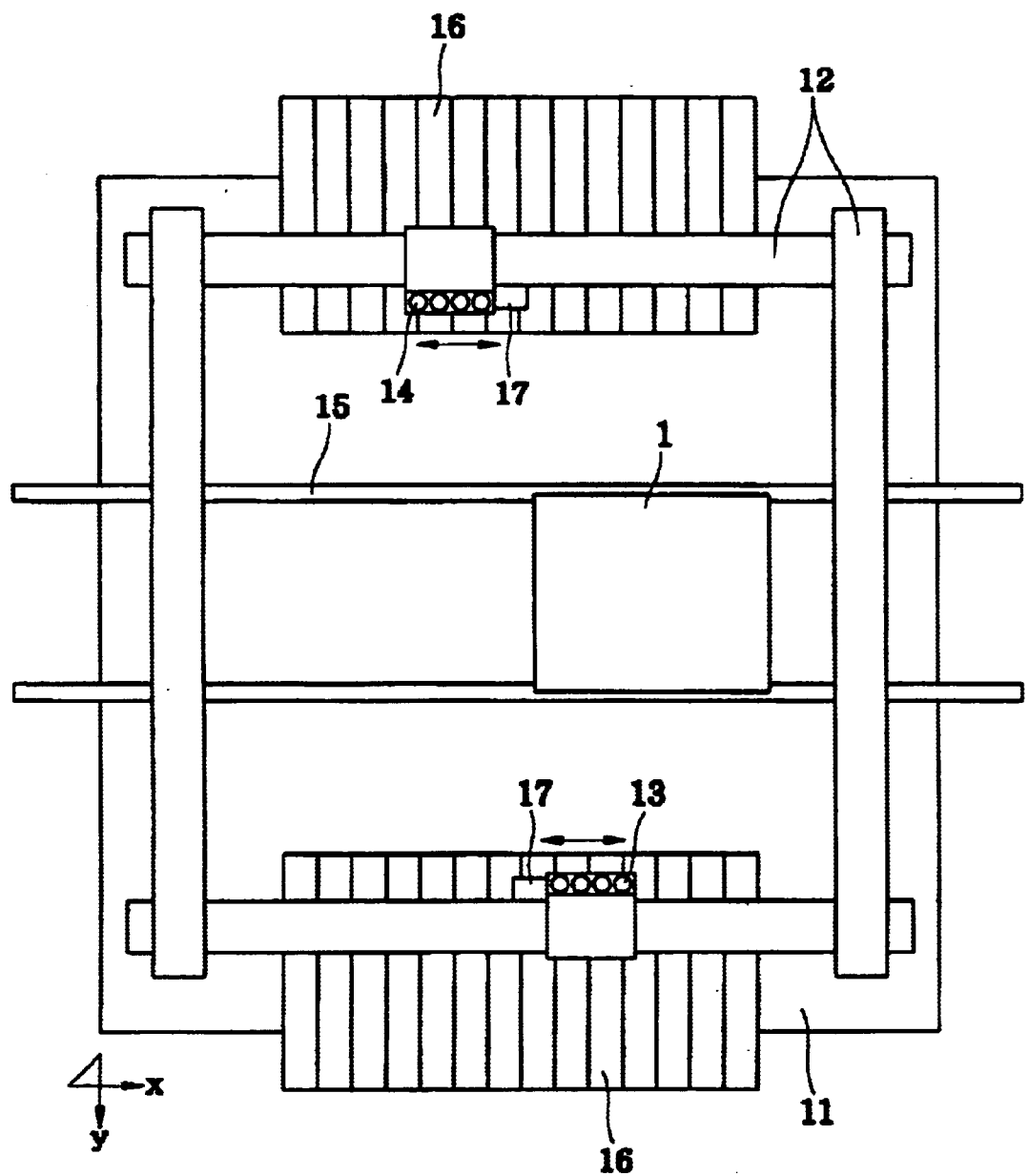
FIG. 2 is a plane view illustrating a surface mounting apparatus of FIG. 1.
Figure 3:
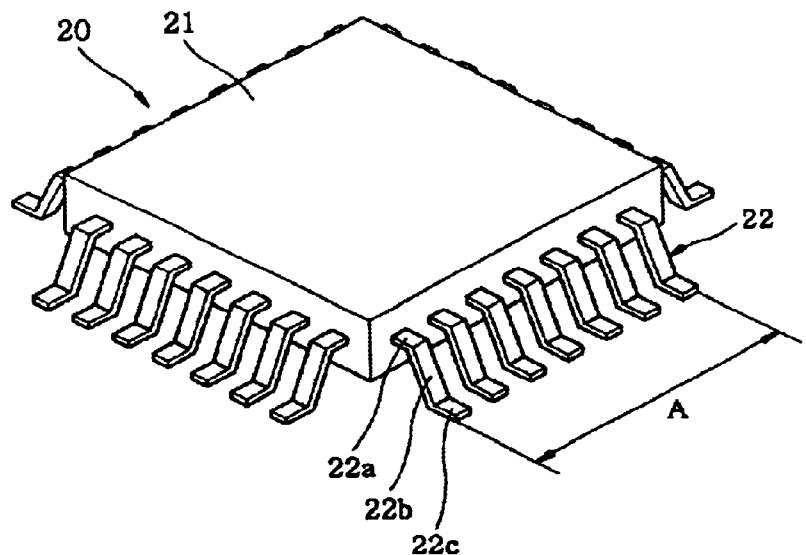
FIG. 3 is a perspective view illustrating the components.
Figure 4:
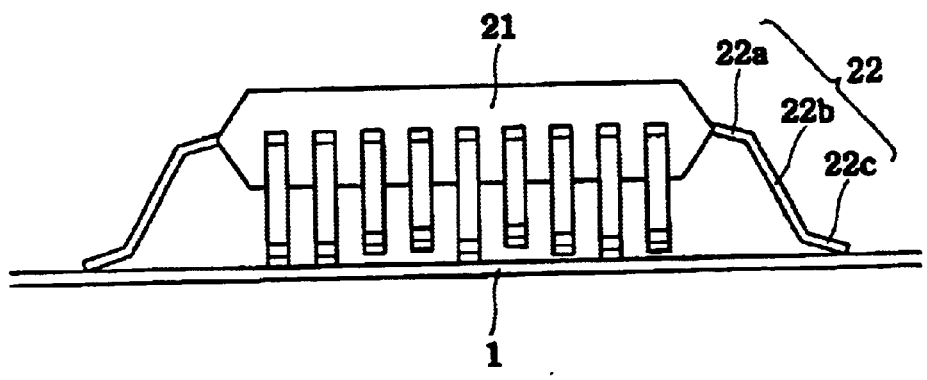
FIG. 4 is a side cross-section view of FIG. 3.
Figure 5:
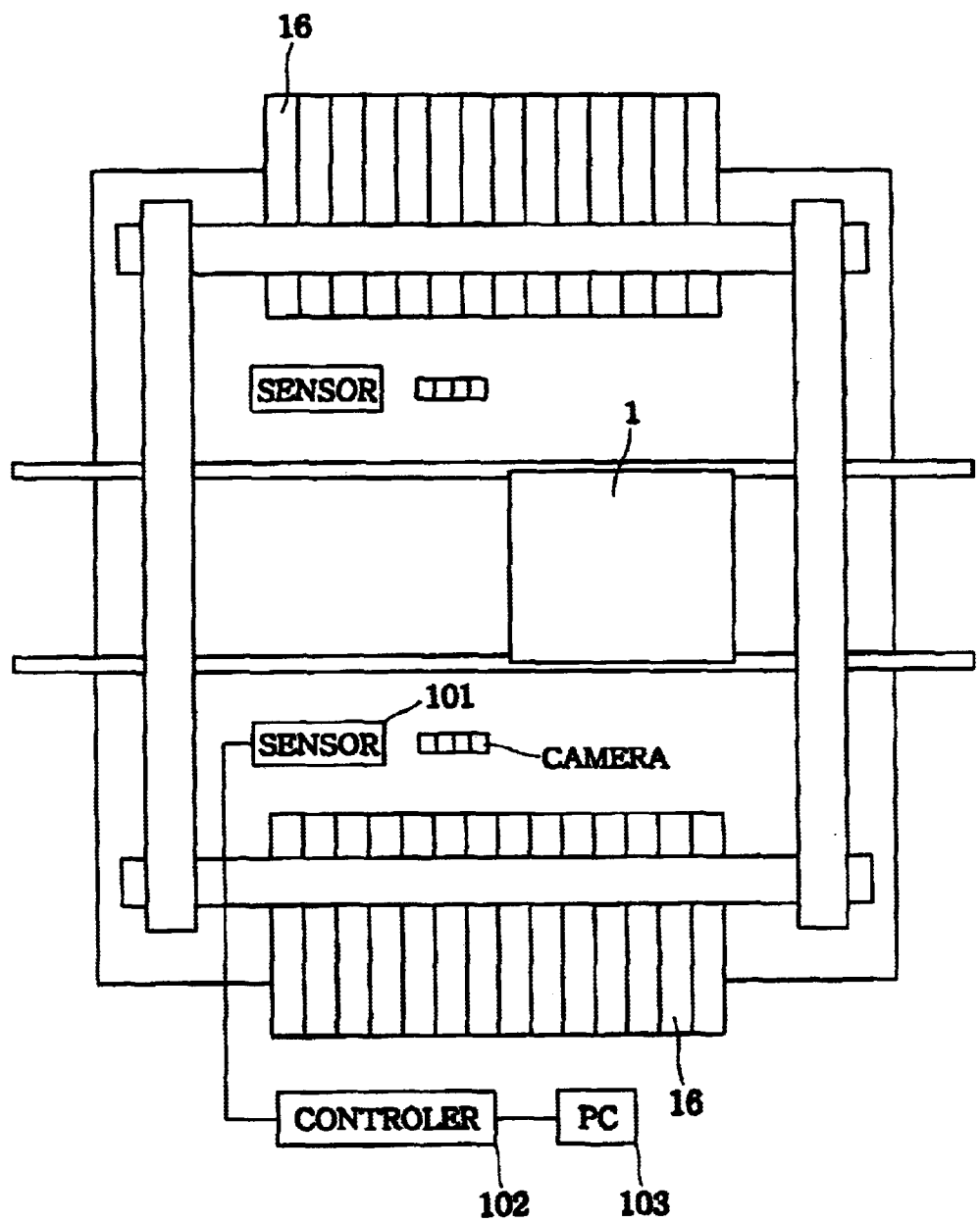
FIG. 5 is an outline view illustrating a coplanartiy inspection apparatus according to the present invention.
Figure 6:
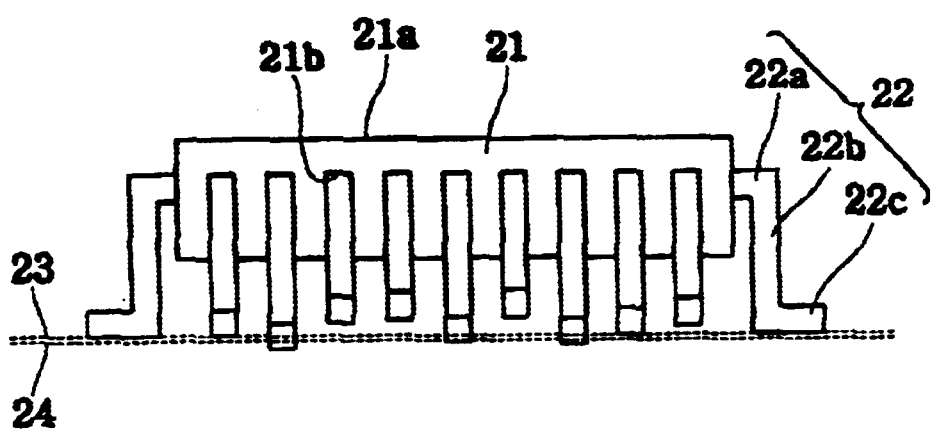

FIG. 5 is a view illustrating a coplanartiy inspection apparatus according to the present invention. As shown in FIG. 5, the coplanarity inspection apparatus comprises: a laser sensor 101; a controller 102 installed to a lower side of a components supplying apparatus 16 with a distance; and a personal computer 103 installed to a predetermined position of a mounter for receiving the data outputted through the controller 102 and then computing the coplanarity.

Here, after picking the components and inspecting the position and alignment state of the components at the vision apparatus, when inspecting the coplanarity again, the laser sensor 101 is used. The laser sensor 10 is constructed by a light receiving portion and a light emitting portion, and a scan is performed in the light emitting portion by the laser and then the coplanarity is transmitted to the light receiving portion. At this time, the data is transmitted to the personal computer 103 installed to the predetermined portion of the mounter through the controller 102 and then the coplanarity is inspected.

Figure 7A:
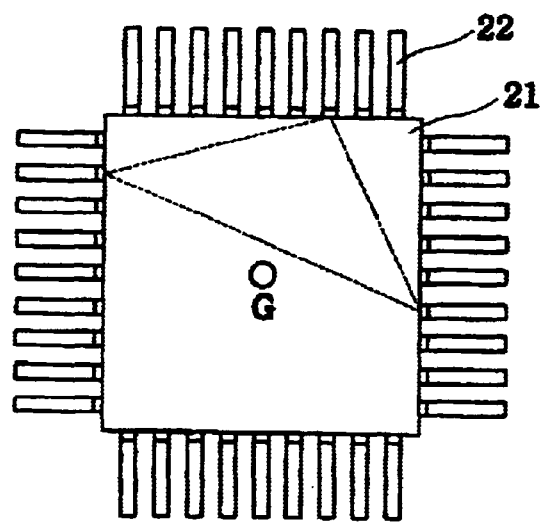
FIGS. 7a and 7b are plane views illustrating a process for forming a reception surface as a reference of the coplanarity inspection of the components.
Figure 7B:
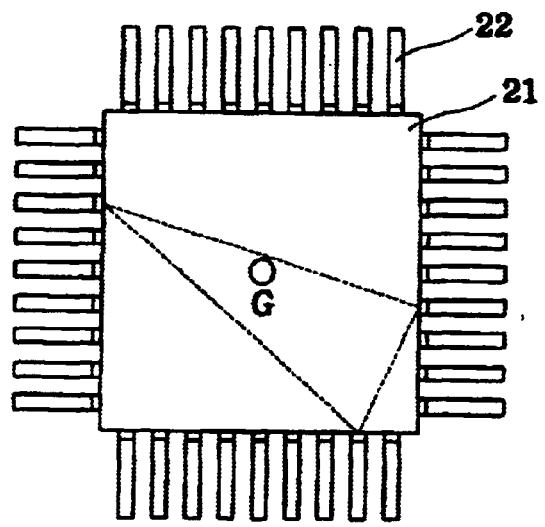

As shown in FIGS. 7a and 7b, in order to explain the above coplanarity inspection method, the construction of the components 20 will be explained in detail. The component 20 comprises a package body 21 and a plurality of leads 22. The Plate type package body 21 comprises an upper surface 21a and a lower surface 21b. The lead comprises a protrusion portion 22a protruded horizontally from the package body 21, an inclination portion 22b extended with slant of a predetermined angle downwardly from the protrusion portion 22a, and a pin portion 22c protruded extendedly again horizontally from the inclination portion 22b.

The components 20 is mounted to the printed circuit board (PCB), that is, its lower surface 21b is positioned opposite to the PCB. In this mounting state, there are three leads among the leads 22 being contacted at a flat surface, that is, the leads positioned at the farthest position from the lower surface 21b exist.

As described above, the surface constructed by the three leads becomes the reception surface 24, the coplanarity is inspected by measuring a distance from the reception surface 24.

FIGS. 7a and 7b are plane views illustrating a process for forming a reception surface as a reference of the coplanarity inspection of the components. As shown in FIGS. 7a and 7b, a center of gravity of a component (generally a center of a component) must be included within a triangle formed by three points of the farthest leads (the lowest leads) from the lower surface 21b and the leads 22 above three points defined as a reception surface 24 become basic plane. (for example, the copolanarity is "0").

The copolanarity inspection method according to the present invention comprises: a first step for confirming a position and an alignment state of the component and then determining a scan path after picking up the component by a head unit; a second step for moving the component into a position capable of inspecting through a fixed laser sensor 101 and scanning the leads; and a third step for inspecting the respective leads of the component in the above scanning step and processing the inspecting data by an algorithm and then inspecting the copolanarity of the component.

In the first step, the position and the alignment state denote a degree that each lead is off from the straight line comprised of the height of leads at one surface of the component.

The method of inspecting coplanarity of electronic components according to the present invention comprises the steps of: obtaining lead height data of one surface of the electronic components; calculating the number of leads by finding gaps between leads; obtaining height data of the respective leads by dividing the number of leads when all leads are contacted, obtaining the respective leads by dividing the leads through a width of the represented lead when two or more leads are contacted, and when all leads are not inspected, discriminating the state as an error and then performing a return process; averaging the data of the respective leads and then providing the average data as a height of a lead; performing a straight line interpolation process from the height of each lead by the method of least squares; calculating an error by calculating a distance of each lead from a straight line; calculating an error by again performing the straight line interpolation process, except for 50% with large errors; and performing a returning process to the value having the largest error.

The third step is a step for inspecting the coplanarity of the components. The coplanarity denotes a distance which is off from the reception surface (formula of a plane) comprised of three leads, when the leads are mounted to the printed circuit board. The method for calculating the coplanarity the components comprises the steps of: computing coordinates X, Y and Z of each lead; calculating three points having the smallest height of the Z-shaft's lead, including the center of gravity of the component; calculating a formula of a plane comprised of the three points; calculating a separated distance of each lead from the formula of the plane calculated in the above step; and performing a returning process the farthest distance of the lead from the formula of the plane.

That is, the third step will be described again as follows. First, the third step comprises the steps of: applying the obtained data to the algorithm; making the represented values corresponding to the respective leads one-to-one to be corresponded by using the inspection data; forming a reference straight line by using the respective represented values; confirming whether the center of gravity of the component is included within the plane formed by selecting the lowest three points of the minimum values of each surface by using an error to the reference straight line of each surface; determining the plane included the three points as a reception surface and if the center of gravity of the component is included in the above step, inspecting the following minimum and determining the plane included three points as the reception surface; computing errors of all leads on the basis of the determined reception surface; and if the error is above an allowable error, processing the error as an error of the coplanarity.

Figure 8:
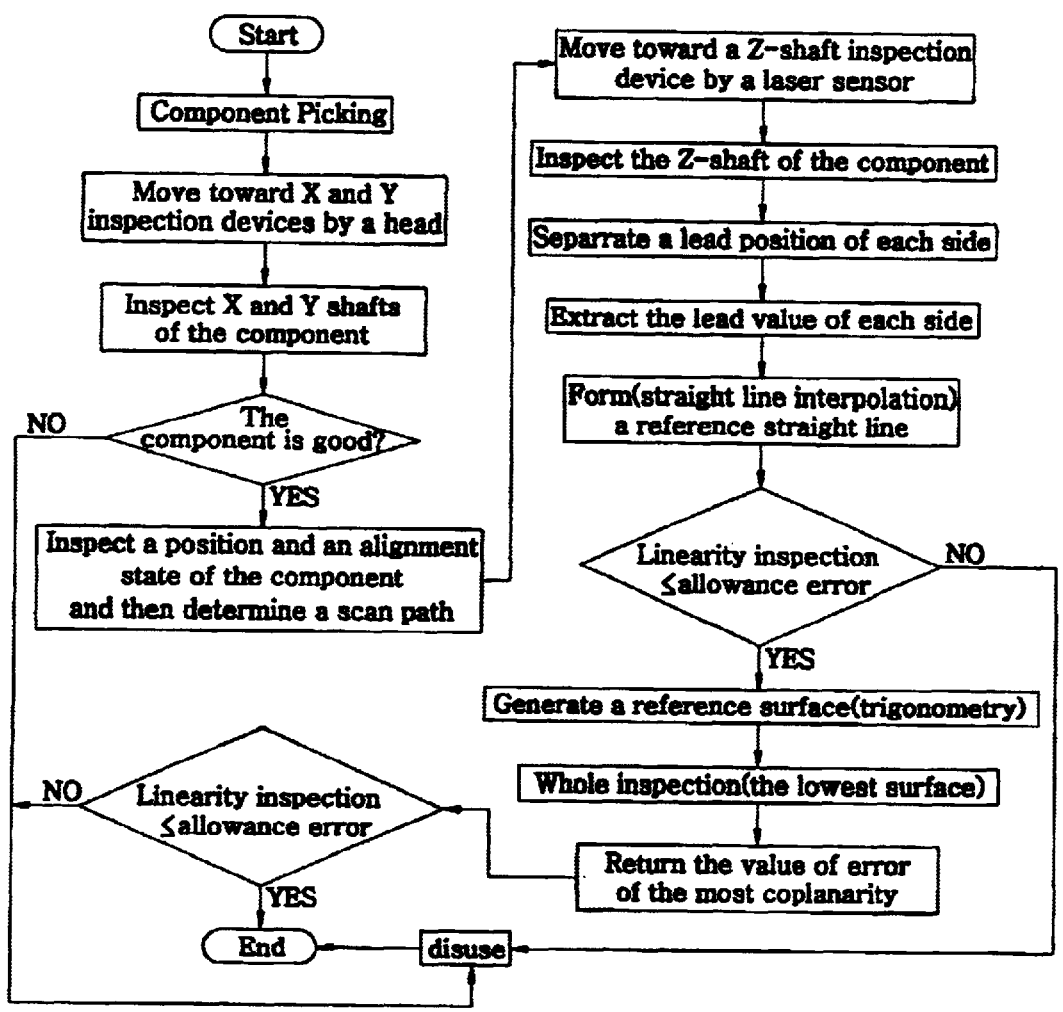
FIG. 8 is a flow chart illustrating a coplanarity inspection apparatus and the method thereof of the components according to the present invention.

Next, as described above, an operation and an effect of the coplanarity inspection system and method according to the present invention will be described with reference to a flow chart of FIG. 8.

First, after the head picks up a component and moves the component toward X and Y inspecting devices, the component is inspected. The badness of the component is discriminated on X and Y coordinates and so in a good component, its position and scan path are determined and a bad component is disused.

The component determined its position and scan path is moved toward a Z-shaft inspecting device for performing the inspection by using a laser sensor 101 and then inspected. Positions according to the respective sides are separated and the lead values according to the respective sides are extracted and thereafter a reference straight line is formed. Thereafter, by inspecting the distance toward the direction of the Z-shaft from the reference straight line, that is, by inspecting the position and alignment of the component, if the value is above an allowable error, the components is disused and if the value is within an allowable error, a reference plane is generated by trigonometry. Thereafter, the lowest surface of the lead, that is, the most error value of the coplanarity is returned by inspecting a reception surface. Thereafter, the coplanarity is inspected and then if the inspection result is above an allowable error, the components is disused and if the inspection result is within an allowable error, the inspection process is finished.

As described above, the coplanarity inspection apparatus and a method thereof according to the present invention, the errors on X and Y coordinates are inspected by using a vision apparatus and then corrected and simultaneously the coplanarity of the component is inspected by using a coplanarity inspection apparatus and corrected, so that the mounting work of the components can be performed smoothly.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalences of such metes and bounds are therefore intended to be embraced by the appended claims.

What is claimed is:

1. In a surface mounting device for picking the electronic components from an electronic component feeding apparatus and then placing the components to a printed circuit board, the surface mounting device comprising:

a vision apparatus including a camera for picking an electronic component from a head and inspecting a position and an alignment state of the electronic components;

a laser sensor including a light receiving part and a light emitting part for inspecting the coplanarity of the electronic components;

a controller for controlling data obtained by the laser sensor; and a computer for computing the coplanarity by receiving the data outputted from the controller.

2. A method for inspecting coplanarity of electronic components comprising:

a first step for picking the electronic components from a component supplying apparatus by using a head unit, making the components move toward a vision apparatus, inspecting X and Y shafts of the electronic components, confirming a position and an alignment state of the components and then determining a scan path;

a second step for making the electronic components move toward a position capable of inspecting and then scanning leads of the components; and a third step for inspecting the Z-shafts of the electronic components and then inspecting the coplanarity of the components by processing the inspected data of the respective leads by algorithm.

3. The method of inspecting coplanarity of electronic components according to claim 2, wherein the first step further comprises the steps of:

obtaining lead height data of one surface of the electronic components;

calculating the number of leads by finding gaps between leads;

obtaining height data of the respective leads by dividing the number of leads when all leads are contacted, obtaining the respective leads by dividing the leads through a width of the represented lead when two or more leads are contacted, and when all leads are not inspected, discriminating the state as an error and then performing a return process;

averaging the data of the respective leads and then providing the average data as a height of a lead;

performing a straight line interpolation process from the height of each lead by the method of least squares;

calculating an error by calculating a distance of each lead from a straight line;

calculating an error by again performing the straight line interpolation process, except for 50% with large errors; and performing a returning process to the value having the largest error.

4. The method of inspecting coplanarity of electronic components according to claim 2, wherein the second step further comprises the steps of:

applying the obtained data to an algorithm;

making the represented values corresponding to the respective leads one-to-one to be corresponded by using the inspection data;

forming a reference straight line by using the respective represented values;

confirming whether the center of gravity G of the component is included within the plane formed by selecting the lowest three points of the minimum values of each surface by using an error to the reference straight line of each surface;

determining the plane included the three points as a reception surface and if the center of gravity of the component is included in the above step, inspecting the following minimum and determining the plane included three points as the reception surface;

computing errors of all leads on the basis of the determined reception surface; and processing the error as an error of the coplanarity, if the error is above an allowable error.

\* \* \* \* \*